(12) United States Patent
Wakabayashi et al.

(10) Patent No.: US 8,230,728 B2
(45) Date of Patent: Jul. 31, 2012

(54) ALCOHOL CONCENTRATION SENSOR DISPOSED IN FUEL TANK OF AUTOMOTIVE VEHICLE

(75) Inventors: Shinji Wakabayashi, Anjo (JP); Hiroshi Nakamura, Nishio (JP); Akikazu Uchida, Kariya (JP); Yukinobu Kajita, Takahama (JP)

(73) Assignee: Denso Corporation, Kariya (JP)

( * ) Notice: Subject to any disclaimer, the term of this patent is extended or adjusted under 35 U.S.C. 154(b) by 435 days.

(21) Appl. No.: 12/143,901

(22) Filed: Jun. 23, 2008

(65) Prior Publication Data

US 2009/0107215 A1   Apr. 30, 2009

(30) Foreign Application Priority Data

Oct. 25, 2007   (JP) .................................. 2007-277718

(51) Int. Cl.
    *G01M 15/00*   (2006.01)
(52) U.S. Cl. ................................................... 73/114.38
(58) Field of Classification Search ................ 73/114.38
    See application file for complete search history.

(56) References Cited

U.S. PATENT DOCUMENTS

| 4,479,116 | A | * | 10/1984 | Kobayashi | .................... | 340/620 |
| 5,861,577 | A | * | 1/1999 | Tamura et al. | ............. | 174/50.56 |
| 6,308,732 | B1 | * | 10/2001 | Herndon | ........................ | 137/560 |

FOREIGN PATENT DOCUMENTS

| JP | 64-53957 | 4/1989 |
| JP | 02-267362 | 11/1990 |

OTHER PUBLICATIONS

Japanese Office Action dated Aug. 18, 2009, issued in corresponding Japanese Application No. 2007-277718, with English translation.

* cited by examiner

*Primary Examiner* — Hezron E Williams
*Assistant Examiner* — Nathaniel Kolb
(74) *Attorney, Agent, or Firm* — Nixon & Vanderhye PC

(57) ABSTRACT

An alcohol density sensor for detecting an alcohol density in mixture fuel composed of petroleum-fuel and alcohol is installed in a fuel tank of an automotive vehicle. The alcohol density sensor includes a pair of electrodes immersed in the mixture fuel and a conductor portion for connecting the electrodes to a control unit having a circuit board. The conductor portion is composed of a first conductor portion integrally formed with the electrode and a second conductor portion connected to the first conductor portion. The first conductor portion is led out of a casing containing the electrodes and liquid-tightly sealed at a first through-hole formed in the casing. The second conductor portion is led out of the fuel tank through a second through-hole formed in the fuel tank. Since the first through-hole is sufficiently sealed to prevent pressurized mixture fuel in the casing from leaking into an inner space of the fuel tank, sealing of the second through-hole can be simplified.

23 Claims, 4 Drawing Sheets

ALCOHOL CONCENTRATION SENSOR DISPOSED IN FUEL TANK OF AUTOMOTIVE VEHICLE

CROSS-REFERENCE TO RELATED APPLICATION

This application is based upon and claims benefit of priority of Japanese Patent Application No. 2007-277718 filed on Oct. 25, 2007; the content of which is incorporated herein by reference.

BACKGROUND OF THE INVENTION

1. Field of the Invention

The present invention relates to an alcohol density sensor for detecting an alcohol content mixed in fuel such as gasoline. The alcohol density sensor is disposed in a fuel tank of an automotive vehicle.

2. Description of Related Art

An example of an alcohol density sensor is disclosed in JP-U-64-53957. An essential portion of the sensor is shown in FIGS. 4A and 4B attached hereto. The sensor includes a pair of electrodes 102 immersed in mixture fuel composed of gasoline and alcohol. The electrodes 102 for detecting an alcohol density in the mixture fuel are connected to a control unit 103 through wires 124 covered with insulator. A casing 104 for containing the alcohol density sensor therein is disposed in a fuel tank. A fuel pump 106 for supplying the mixture fuel to an internal combustion engine through a fuel supply passage 105 of the casing 104 is supported by a supporting member 106 fixed to a upper wall 107 of the fuel tank.

A pair conductor portions 111 integrally formed with the electrodes 102 is supported by an insulating resin member 113 contained in the casing 104. The pair of conductor portions 111 is connected to a pair of bare wires 121 of the insulator-covered wires 124 in the casing 104. The insulator-covered wires 124 are led out of the casing 104 through through-holes 114 and connected to the control unit 103. Small spaces between the through-holes 114 and the insulator-covered wires 124 are sealed with seal members 125. The seal members 125 prevent fuel pressurized by the fuel pump 101 from leaking to an outside of the casing 104 along the electrodes 102 and the conductor portions 111. Electric resistance in the mixture fuel becomes lower as an alcohol density in the mixture fuel becomes higher. Accordingly, the alcohol density can be detected by measuring the electric resistance between the pair of electrodes 102.

In the conventional sensor described above, a following problem is involved. Pressure of the mixture fuel in the casing 104 including the fuel supply passage 105 is higher than a pressure in the fuel tank (which is the same as atmospheric pressure), because the mixture fuel flowing through the fuel supply passage 105 is pressurized by the fuel pump 101. Therefore, the high pressure fuel may flow through a small gap between the bare wires 121 and the insulator covering the wire 124. There is a possibility that the mixture fuel leaked from the casing 104 may reach the control unit 103 that is positioned outside the fuel tank.

SUMMARY OF THE INVENTION

The present invention has been made in view of the above-mentioned problem, and an object of the present invention is to provide an improved alcohol density sensor, in which possibility of fuel leakage to an outside of the fuel tank is eliminated.

The alcohol density sensor according to the present invention is installed in a fuel tank of an automotive vehicle which contains mixture fuel composed of gasoline or light oil (referred to as petroleum-fuel) and alcohol. The alcohol density sensor includes a pair of electrodes, a capacitance between which varies according to dielectric constant of the mixture fuel. The electrodes are contained in a casing disposed in a fuel tank and exposed to the mixture fuel sent from a fuel pump which is also disposed in the fuel tank. A conductor portion is integrally formed with the electrodes and is electrically connected to a circuit board of an control unit disposed outside the fuel tank.

The conductor portion is composed of a first conductor portion that is led out of the casing into an inner space of the fuel tank through a first through-hole formed in the casing and a second conductor portion that is lead out of the inner space of the fuel tank to an outside of the fuel tank through a second through-hole formed in the fuel tank. A small space between the first conductor portion and the first through-hole is liquid-tightly sealed. A small space between the second conductor portion and the second through-hole is also sealed.

The second conductor portion may be replaced with a conductor covered with insulator, and wires exposed by peeling off a portion of the insulator are electrically connected to the first conductor at a position outside the casing. Alternatively, the wires exposed by peeling off the insulator may be further extended so that the wires go through the first through-hole into the casing and electrically connected to the first conductor portion at a position inside the casing.

The first conductor or the bare wires exposed by peeling off the insulator go through the first through-hole, and the first through-hole is liquid-tightly sealed. Accordingly, the mixture fuel pressurized by a fuel pump in the casing does not is leak into the inner space of the fuel tank. Therefore, the mixture fuel does not leak out of the fuel tank only by providing a simple seal for the second through-hole. Further, since no conductor covered with insulator goes through the first through-hole, the sealing at the first through-hole can be effectively made. There is no possibility that the mixture fuel leaks through a small space between conductor wires and the insulator covering the conductor wires.

According to the present invention, the alcohol density sensor can be easily installed in the fuel tank without causing leakage of the mixture fuel. Other objects and features of the present invention will become more readily apparent from a better understanding of the preferred embodiments described below with reference to the following drawings.

DETAILED DESCRIPTION OF THE PREFERRED EMBODIMENTS

A first embodiment of the present invention will be described with reference to FIG. 1. Mixture fuel is formed by mixing a certain amount of alcohol, such as ethanol or methanol, with the petroleum-fuel. Such mixture fuel is supplied, for example, to an internal combustion engine having an electronically controlled fuel injection and ignition system. The internal combustion engine, to which the mixture fuel is supplied, may be a four-cycle engine. Mixture fuel is mixed with a proper amount of air and supplied to the engine from the fuel injector installed in each cylinder or an intake manifold. The air-fuel mixture supplied to each cylinder is ignited by a spark plug installed in each cylinder.

Mixture fuel contained in a fuel tank is pressurized by a fuel pump and is sent to engine cylinders through a delivery pipe. An alcohol density sensor is installed in the fuel tank. The alcohol density sensor may be included as a component of a pump module installed in the fuel tank. The pump module may include a fuel pump for pressurizing fuel and a fuel amount sensor for detecting an amount of fuel in the fuel tank.

Figure 1:
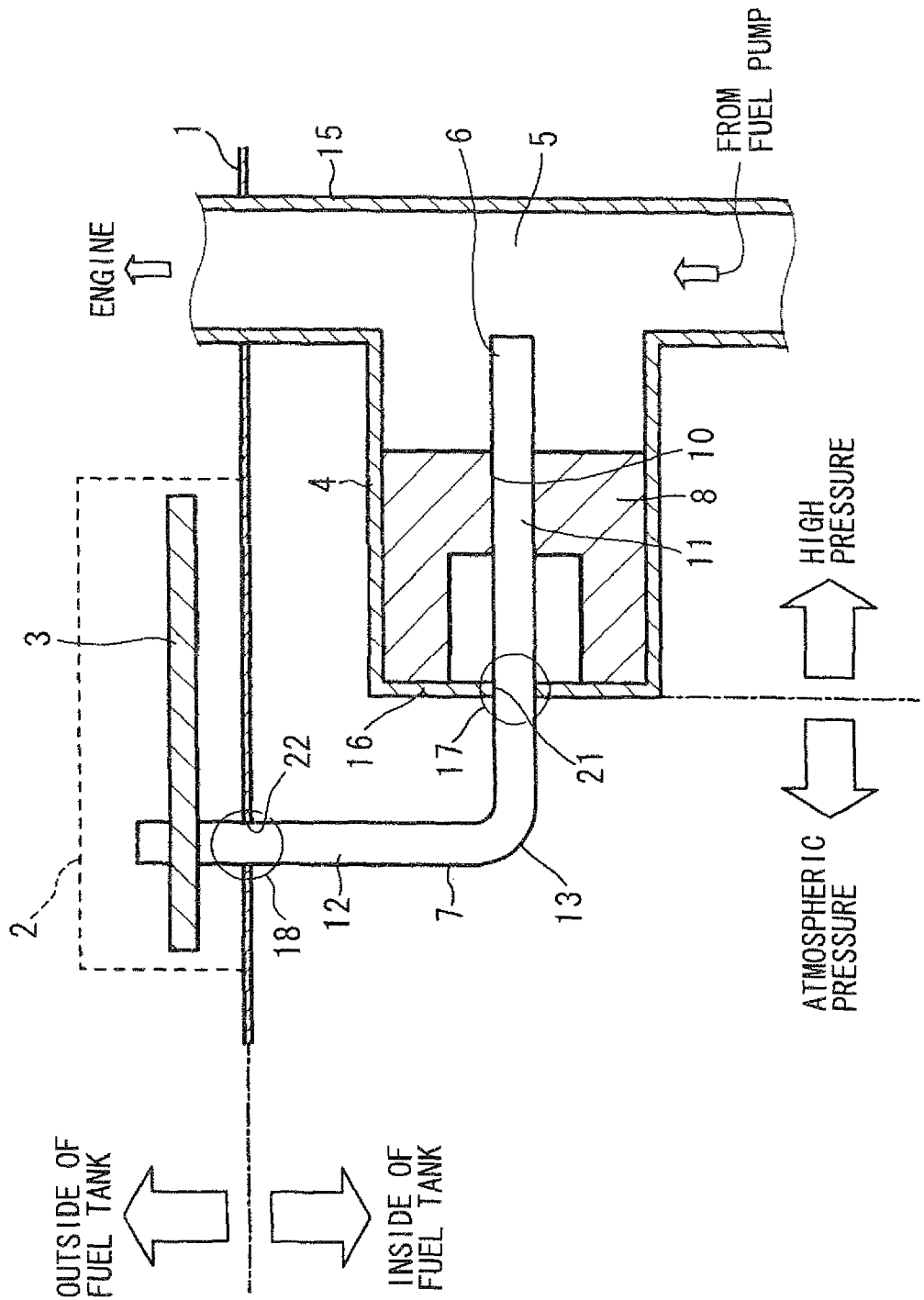
FIG. 1 is a schematic cross-sectional view showing an alcohol density sensor disposed in a fuel tank, as a first embodiment of the present invention.

As shown in FIG. 1, the alcohol density sensor including electrodes 6 (a pair of electrodes) and a conductor portion 7 (that includes a pair of conductors) integrally formed with the electrodes 6 and a casing 4 is installed in a fuel tank having an upper wall 1. The alcohol sensor functions as a capacitor-type sensor that detects a capacitance between a pair of electrodes. The electrodes 6 are electrically connected to a circuit board 3 of a control unit 2 which is disposed outside the fuel tank. Mixture fuel pressurized by a fuel pump disposed in the fuel tank is sent to the engine through a fuel supply passage 5 formed in the casing 4.

The electrodes 6 are exposed and immersed in the mixture fuel in the casing 4. The conductor portion 7 is composed of a first conductor portion 11 that is led out of the casing 4 through a first through-hole 21 and a second conductor portion 12 that is led out of the fuel tank through a second through-hole 22 formed in the upper wall 1 of the fuel tank. The conductor portion 7 is bent, forming an L-shape between the first conductor portion 11 and the second conductor portion 12.

The casing 4 includes an inner space containing an insulating resin member 8 that supports the electrodes 6 and the first conductor portion 11. The fuel supply passage 5, through which the mixture fuel pressurized by the fuel pump is supplied to the engine, is formed in the casing 4. The first conductor portion 11, supported in a supporting hole 10 of the insulating resin member, is led out of the casing 4 through the first through-hole 21 formed in an end wall 16 of the casing 4. A small space between the first through-hole 21 and the first conductor portion 11 is liquid-tightly sealed, forming a first seal portion 17, so that the pressurized fuel does not leak through the first through-hole 21 into the fuel tank which is at the atmospheric pressure. The second conductor portion 12 is led out through the second through-hole 22 which is sealed, forming a second seal portion 18.

The pair of electrodes 6 immersed in the mixture fuel is electrically connected to the circuit board 3 of the control unit 2 through the conductor portion 7. A dielectric constant varies according to an alcohol density in the mixture fuel, and the dielectric constant is detected based on a capacitance between the pair of electrodes 6. More particularly, the capacitance increases according to increase of the alcohol density in the mixture fuel. The circuit board 3 includes an oscillator circuit generating a frequency (F) and a frequency/voltage converter circuit that converts the frequency (F) to a signal voltage. The dielectric constant of the mixture fuel is represented by a signal voltage that is fed from the control unit 2 to an electronic control unit (ECU) mounted on the vehicle.

The ECU (not shown in drawings) is composed of a microcomputer including a central processing unit, and other associated components such as memory devices (ROM and RAM) for storing a control program and data, a power source circuit, and input/output circuits. Various signals are fed to the ECU from sensors, such as a crank angle sensor, an accelerator sensor detecting an opening degree of an accelerator, a temperature sensor detecting cooling water temperature, a temperature sensor detecting intake-air temperature, and the alcohol density sensor. Upon turning on an ignition switch, the ECU controls operation of the engine based on the control program stored therein. That is, an amount of intake-air, an amount of fuel injected, an air-fuel ratio, ignition timing and so on are controlled so that they become target values. Upon turning off the ignition switch, the control performed by the ECU is terminated.

The mixture fuel contained in the fuel tank is pressurized by the fuel pump and supplied to the engine through the fuel supply passage 5 of the casing 4. The fuel supply passage 5 is connected to injectors, each corresponding to each cylinder, through a delivery pipe. The ECU detects the alcohol density in the mixture fuel based on the signal voltage sent from the control unit 2. The ECU controls operation of the engine, including the air-fuel ratio, fuel injection and ignition, based on the detected alcohol density.

Advantages attained in the first embodiment described above will be summarized below. The first conductor portion 11 that is not covered with an insulating layer is led out through the first through-hole 21, and the first through-hole 21 is liquid-tightly sealed, forming the first seal portion 17. Since the first conductor portion 11 is not covered with an insulator film or layer, i.e., the first conductor portion 11 is a bare conductor, the sealing between the first conductor portion 11 and the first through-hole 21 can be made very tightly. Therefore, a passage, through which the pressurized mixture fuel in the casing 4 leaks to an inside space of fuel tank at the atmospheric pressure, is eliminated. Accordingly, the second seal portion 18 formed in the upper wall 1 of the fuel tank between the second conductor portion 12 and the second through-hole 22 can be simplified. That is, the second seal portion 18 can be made easily without using an expensive sealing material such as rubber having a high endurance against fuel.

The second conductor portion 12 is also a bare conductor integrally made with the first conductor portion 11. The second conductor portion 12 is led out from the inner space of the fuel tank through the second through-hole 22 formed in the upper wall 1 of the fuel tank, forming the second seal portion 18. Accordingly, the electrodes 6 are easily connected to the circuit board 3 of the control unit 2 through the conductor portion 7 (composed of the first conductor portion 11 and the second conductor portion 12) integrally formed with the electrodes 6 without using insulated lead wires.

Figure 2:
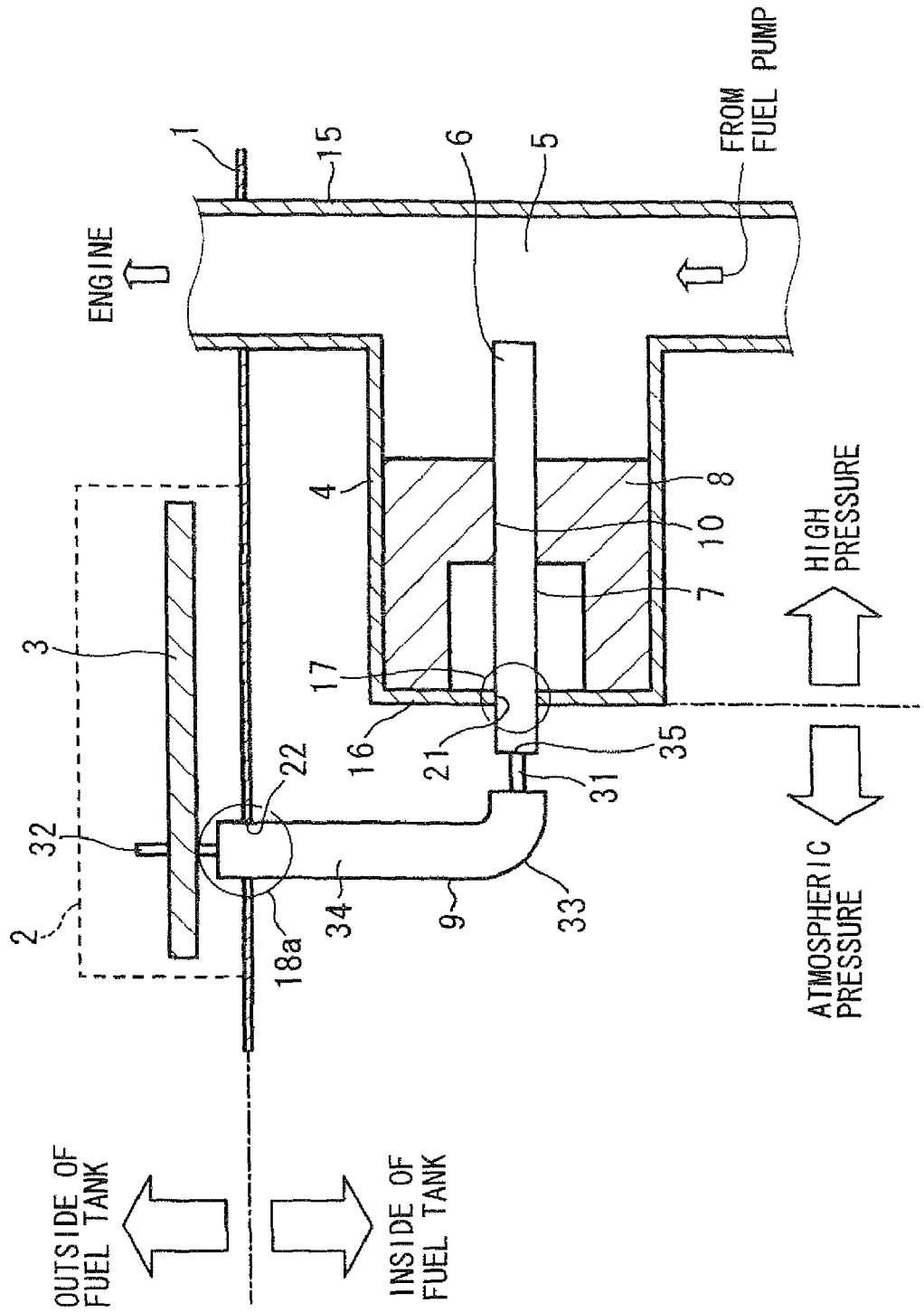
FIG. 2 is a schematic cross-sectional view showing an alcohol density sensor disposed in a fuel tank, as a second embodiment of the present invention.

A second embodiment of the present invention is shown in FIG. 2. In this embodiment, the conductor portion 7 integrally formed with the electrodes 6 is composed of only the first conductor portion 11. The second conductor portion 12 used in the first embodiment is replaced with a conductor 9 (having two conductor wires) covered with insulator 34. The insulator 34 covering the conductor 9 is peeled off at both ends, exposing first conductor wires 31 at one end and second conductor wires 32 at the other end. The conductor 9 covered with insulator 34 has a portion 33 bent in an L-shape.

The first conductor portion 11 is led out through the first through-hole 21 and sealed, forming the first seal portion 17. The first conductor wires 31 are electrically connected to the first conductor portion 11 at a position outside the casing 4, forming an external connecting end 35. The conductor 9 covered with insulator 34 is led out through the second through-hole 22 and sealed, forming a second seal portion 18a. The second conductor wires 32 are electrically connected to the circuit board 3 of the control unit 2. The insulator 34 covering the conductor 9 is made of insulating materials, such as fluorine resin, silicone rubber or silicone resin. Other structures of the second embodiment are the same as those of the first embodiment.

The first conductor portion 11 that is not covered with insulator is led out from the casing 4, and a space between the first through-hole 21 and the first conductor portion 11 is sealed, forming the first seal portion 17. Since the first conductor portion 11 is not covered with an insulator layer, the liquid-tight first seal portion 17 is easily formed. The passage of the pressurized fuel from the inside space of the casing 4 to the inner space of the fuel tank which is substantially at the atmospheric pressure is eliminated in the same manner as in the first embodiment. Accordingly, the second seal portion 18a that seals a small space between the insulator film 34 of the conductor 9 and the second through-hole 22 can be easily formed.

Figure 3:
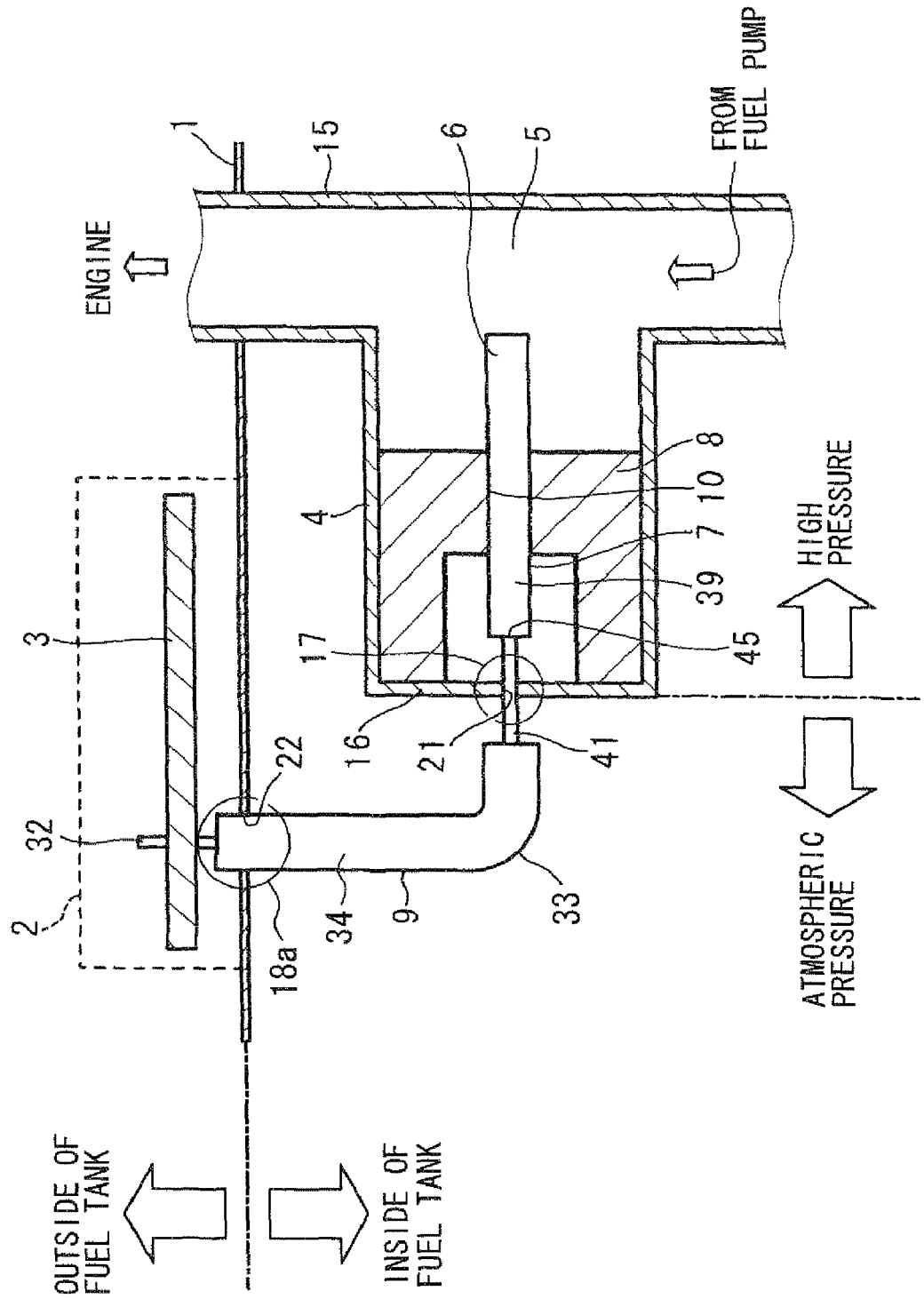
FIG. 3 is a schematic cross-sectional view showing an alcohol density sensor disposed in a fuel tank, as a third embodiment of the present invention.
Figure 4A:
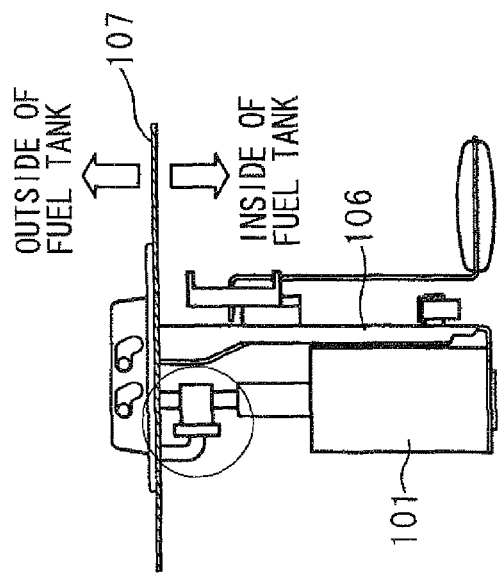
FIGS. 4A and 4B are schematic views showing a conventional alcohol density sensor.
Figure 4B:
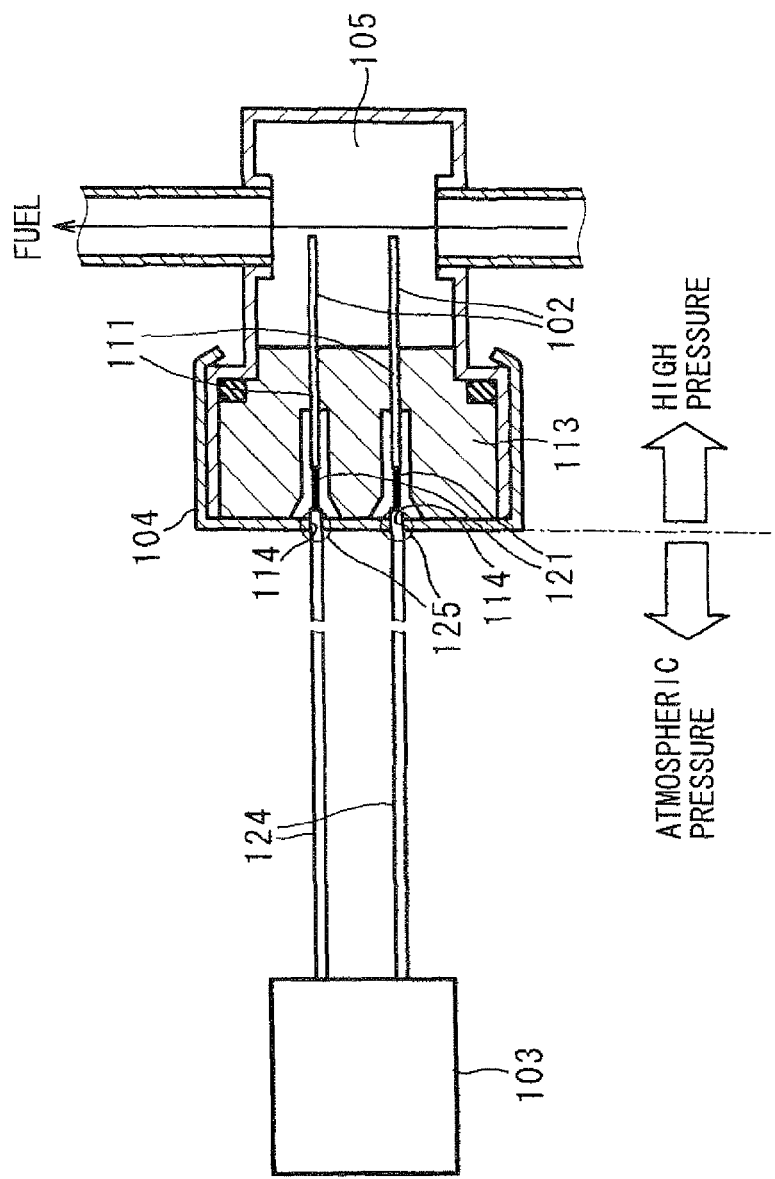

A third embodiment of the present invention is shown in FIG. 3. In this embodiment, the first conductor portion 11 used in the second embodiment is replaced with a first conductor portion 39 which is a little shorter than the first conductor portion 11 used in the second embodiment. Both ends of the insulator 34 covering the conductor 9 are removed to expose the first conductor wires 41 at one end and the second conductor wires 32 at the other end. The first conductor wires 41 are inserted into the inner space of the casing 4 through the first through-hole 21 and electrically connected to the first conductor portion 39, forming an internal connecting end 45. The second conductor wires 32 are electrically connected to the circuit board 3 of the control unit 2. Other structures in this third embodiment are the same as those of the second embodiment.

A small space between the conductor wires 41 not covered with the insulator 34 and the first through-hole 21 is sealed, forming the first seal portion 17. Therefore, pressurized mixture fuel in the casing 4 does not leak through the first seal portion 17 to the inner space of the fuel tank where the pressure is substantially at the atmospheric pressure. Accordingly, the second seal portion 18a in the upper wall 1 of the fuel tank can be simplified, as in the first and the second embodiments.

The present invention is not limited to the embodiments described above, but it may be variously modified. For example, an electric resistance of the mixture fuel between the pair of electrodes 6 may be detected in place of the capacitance between the pair of electrodes. The alcohol density in the mixture fuel can be similarly detected based on the electric resistance between the pair of electrodes 6. Though the alcohol density sensor is connected to the casing 4 supporting the fuel pump in the foregoing embodiments, it is also possible to connect the casing 4 containing the alcohol density sensor therein to the fuel tank independently from the fuel pump. It is also possible to detect the alcohol density in the mixture fuel composed of light oil and alcohol.

While the present invention has been shown and described with reference to the foregoing preferred embodiments, it will be apparent to those skilled in the art that changes in form and detail may be made therein without departing from the scope of the invention as defined in the appended claims.

What is claimed is:

1. An alcohol concentration sensor for detecting an alcohol concentration in mixture fuel composed of petroleum-fuel and alcohol, the alcohol concentration sensor comprising:
electrodes immersed in the mixture fuel contained in a fuel tank of an automotive vehicle;
a conductor portion including a first conductor portion and a second conductor portion, the first conductor portion being integrally formed with the electrodes; and
a casing disposed in the fuel tank, the casing containing the electrodes and the first conductor portion, wherein:
the first conductor portion is disposed in the casing and is led out of the casing to an inner space of the fuel tank and the second conductor portion extends from the first conductor portion, through the inner space of the fuel tank, and extends to an outside of the fuel tank, so that the conductor portion extends continuously as a one-piece conductor without connectors or junctions from the integral formation with the electrodes to the outside of the fuel tank, and
the entire conductor portion, including each of the first conductor portion and the second conductor portion, is a bare conductor that is not covered with an insulating layer.

2. The alcohol concentration sensor as in claim 1, wherein:
the alcohol concentration sensor further includes a control unit disposed outside the fuel tank; and the electrodes are electrically connected to the control unit through the conductor portion.

3. The alcohol concentration sensor as in claim 2, wherein:
the control unit includes a circuit board for detecting the alcohol concentration; and the conductor portion is electrically connected to the circuit board.

4. The alcohol concentration sensor as in claim 3, wherein:
the casing includes a first through-hole through which the first conductor portion is led out; and the fuel tank includes a second through-hole through which the second conductor portion is led out.

5. The alcohol concentration sensor as in claim 4, wherein:
a small space between the first conductor portion and the first through-hole is liquid-tightly sealed.

6. The alcohol concentration sensor as in claim 1, wherein:
a fuel pump is disposed in the fuel tank, and the casing includes a fuel supply passage through which the mixture fuel pressurized by the fuel pump flows.

7. The alcohol concentration sensor as in claim 1, wherein:
the first conductor portion is led out of the casing through a first through-hole and the second conductor portion is led out of the fuel tank through a second through-hole formed in an upper wall of the fuel tank, the conductor portion being bent, forming an L-shape between the first through-hole and the second through-hole, the first conductor portion being liquid-tightly sealed in the first through-hole, forming a first seal portion, and the second conductor portion being sealingly disposed in the second through-hole forming a second seal portion.

8. An alcohol concentration sensor for detecting an alcohol concentration in mixture fuel composed of petroleum-fuel and alcohol, the alcohol concentration sensor comprising:
electrodes immersed in the mixture fuel contained in a fuel tank of an automotive vehicle;
a conductor portion integrally formed with the electrodes, the conductor portion being a bare conductor that is not covered with an insulating layer;
a conductor covered with insulator electrically connected to the conductor portion, so that the conductor portion has one end integrally formed with the electrodes and another end electrically connected with the conductor that is covered with insulator; and a casing disposed in the fuel tank, the casing containing the electrodes and the conductor portion, wherein:

the conductor portion is led out of the casing to an inner space of the fuel tank, the conductor portion having a first seal portion with the casing where the conductor portion penetrates through the casing to the inner space of the fuel tank, so that the first seal portion is provided only at a position where the conductor portion penetrates through the casing and where the conductor portion is not covered by an insulating layer;

the conductor portion being electrically connected to a conductor wire of the conductor covered with insulator within the fuel tank; and the conductor covered with insulator is led out of the inner space of the fuel tank to an outside of the fuel tank.

9. The alcohol concentration sensor as in claim 8, wherein the alcohol concentration sensor further includes a control unit disposed outside the fuel tank; and the electrodes are electrically connected to the control unit through the conductor portion and the conductor covered with insulator.

10. The alcohol concentration sensor as in claim 9, wherein:

the control unit includes a circuit board for detecting the alcohol concentration; and the conductor covered with insulator is electrically connected to the circuit board.

11. The alcohol concentration sensor as in claim 8, wherein:

insulator of the conductor covered with insulator is partially peeled off to expose a conductor member and to electrically connect the conductor member to the conductor portion led out of the casing.

12. The alcohol concentration sensor as in claim 11, wherein:

the casing includes a first through-hole through which the conductor portion is led out and fuel tank includes a second through-hole through which the conductor covered with insulator is led out.

13. The alcohol concentration sensor as in claim 12, wherein:

a small space between the conductor portion and the first through-hole is liquid-tightly sealed.

14. The alcohol concentration sensor as in claim 8, wherein:

a fuel pump is disposed in the fuel tank, and the casing includes a fuel supply passage through which the mixture fuel pressurized by the fuel pump flows.

15. The alcohol concentration sensor as in claim 8, wherein:

the conductor portion is led out of the casing through a first through-hole and sealed to form said first seal portion, and the conductor covered with insulator is led out of the fuel tank through a second through-hole and sealed, forming a second seal portion.

16. An alcohol concentration sensor for detecting an alcohol concentration in mixture fuel composed of petroleum-fuel and alcohol, the alcohol concentration sensor comprising:

electrodes immersed in the mixture fuel contained in a fuel tank of an automotive vehicle;

a conductor portion integrally formed with the electrodes, the conductor portion being a bare conductor that is not covered with an insulating layer;

a conductor covered with insulator electrically connected to the conductor portion, so that the conductor portion has one end integrally formed with the electrodes and another end electrically connected with the conductor that is covered with insulator; and a casing disposed in the fuel tank, the casing containing the electrodes and the conductor portion, wherein:

the conductor covered with insulator is led out of the inner space of the fuel tank to an outside of the fuel tank, and the conductor covered with insulator includes first conductor wires extended into the casing and electrically connected to the conductor portion within the casing, and second conductor wires exposed on an outside of the fuel tank, and the first conductor wires are inserted into the casing through a first through-hole to be electrically connected with the conductor portion, the first conductor wires are not covered with an insulator and are sealed in the first through-hole to form a first seal portion, so that the first seal portion is provided only at a position where the first conductor wires penetrate through the casing and where the first conductor wires are not covered by an insulator.

17. The alcohol concentration sensor as in claim 16, wherein:

the alcohol concentration sensor further includes a control unit disposed outside the fuel tank; and the electrodes are electrically connected to the control unit through the conductor portion and the conductor covered with insulator.

18. The alcohol concentration sensor as in claim 17, wherein:

the control unit includes a circuit board for detecting the alcohol concentration; and the second conductor wires are electrically connected to the circuit board.

19. The alcohol concentration sensor as in claim 16, wherein:

the first conductor wires are exposed by peeling off the insulator covering the conductor covered with insulator and extended into the casing.

20. The alcohol concentration sensor as in claim 19, wherein:

the casing includes a first through-hole thorough which the first conductor wires are extended into the casing; and the fuel tank includes a second through-hole through which the conductor covered with insulator is led out to an outside of the fuel tank.

21. The alcohol concentration sensor as in claim 20, wherein:

a small space between the first conductor wires and the first through-hole is liquid-tightly sealed.

22. The alcohol concentration sensor as in claim 16, wherein:

a fuel pump is disposed in the fuel tank, and the casing includes a fuel supply passage through which the mixture fuel pressurized by the fuel pump flows.

23. The alcohol concentration sensor as in claim 16, wherein:

the conductor covered with insulator is led out of the fuel tank through a second through-hole and sealed, forming a second seal portion.

* * * * *